US006569229B1

(12) United States Patent
Buri et al.

(10) Patent No.: US 6,569,229 B1
(45) Date of Patent: May 27, 2003

(54) LOW-FREEZING POINT FORMULATION CONTAINING PHENOL DERIVATIVES

(75) Inventors: Matthias Buri, Rothrist (CH); Patrick Schwarzentruber, Starrkirch-Will (CH)

(73) Assignee: Omya AG, Oftringen (CH)

( * ) Notice: Subject to any disclaimer, the term of this patent is extended or adjusted under 35 U.S.C. 154(b) by 0 days.

(21) Appl. No.: 09/868,603

(22) PCT Filed: Dec. 14, 1999

(86) PCT No.: PCT/EP99/09931

§ 371 (c)(1),
(2), (4) Date: Jul. 31, 2001

(87) PCT Pub. No.: WO00/36913

PCT Pub. Date: Jun. 29, 2000

(30) Foreign Application Priority Data

Dec. 21, 1998 (DE) .......................................... 198 59 136

(51) Int. Cl.[7] .............................................. A01N 31/08
(52) U.S. Cl. .................. 106/15.05; 106/16; 106/18.35; 106/499; 106/500; 162/161; 514/731
(58) Field of Search ............................... 106/15.05, 16, 106/18.35, 499, 500; 162/161; 514/731

(56) References Cited

U.S. PATENT DOCUMENTS

| | | | |
|---|---|---|---|
| 3,824,190 A | 7/1974 | Winicov et al. ............ 514/736 |
| 5,147,884 A | * 9/1992 | Diehl et al. ................. 514/365 |
| 5,256,401 A | * 10/1993 | Duckenfield et al. ......... 424/49 |
| 5,462,681 A | * 10/1995 | Gutzmann et al. .......... 508/513 |
| 5,837,274 A | * 11/1998 | Shick et al. ................. 424/405 |
| 6,019,941 A | * 2/2000 | Porcello ....................... 422/37 |

FOREIGN PATENT DOCUMENTS

| | | |
|---|---|---|
| DE | 2063631 | 7/1971 |
| DE | 2732441 | 2/1979 |
| DE | 2816050 | 10/1979 |
| EP | 0553628 | 8/1993 |
| EP | 0414309 | 1/1996 |
| GB | 872900 | 7/1959 |
| JP | 8-2353404 | 10/1996 |
| WO | 98/17773 | * 4/1998 |

OTHER PUBLICATIONS

Derwent Abstract No. 1977–34539Y, abstract of Canada Patent Specification No. 1061675 (Apr. 1979).*
Derwent Abstract No. 1989–318136, abstract of Spain Patent Specification No. 2006998 (May 1989).*
O'Connor et al., "Phenolic Compounds," Disinfection, Sterilization, and Preservation, Lea & Febiger (Philidelphia, USA), p. 204–224, (Jun. 20, 1991).

* cited by examiner

Primary Examiner—Anthony J. Green
(74) Attorney, Agent, or Firm—Jenkins & Wilson, P.A.

(57) ABSTRACT

The present invention relates to an aqueous formulation containing phenol and/or phenol derivatives having a low freezing point and anti-microbial activity.

37 Claims, No Drawings

LOW-FREEZING POINT FORMULATION CONTAINING PHENOL DERIVATIVES

TECHNICAL FIELD

The present invention relates to an aqueous formulation containing phenol and/or phenol derivatives having a low freezing point and anti-microbial activity.

RELATED ART

Especially if they are used as preservatives in the technical area such as in highly concentrated pigment slurries but also in general if used in a range of pH 7–10.5, phenol derivative formulations have shortcomings. Phenol, alkyl-substituted and aryl-substituted phenols, halogenated phenols as well as cresols and halogenated cresols and the alkali salts thereof are known as anti-fungal and anti-bacterial agents in protective and curative areas. Most of the formulations with these phenol derivatives are poorly water soluble, poorly water miscible or too alkaline for water soluble alkali salt formulations for later use and, therefore, have an adverse effect on the product to be protected or have a freezing point of 0° C. or slightly below 0° C. In particular, o-phenylphenol and sodium o-phenylphenolate as well as potassium o-phenylphenolate are known as anti-fungal agents for wood but also as preservatives for pigment slurries. o-Phenylphenol, sodium o-phenylphenolate and potassium o-phenylphenolate are available form of a powder. o-Phenylphenol is also available in aliphatic glycols such as for example in a solution of 60% by wt. in monopropylene glycol. Sodium o-phenylphenolate is commercially available as a 25% by wt. sodium hydroxide solution and as a 35–38% by wt. emulsion wherein high amounts of emulsifying agents are used for its stabilization. Potassium o-phenylphenolate is commercially available as a 35–39% by wt. potassium hydroxide in water solution. In the form of a powder, o-phenylphenol may not be handled easily. Further, o-phenylphenol is almost insoluble in water and, therefore, it is difficult to mix it into an aqueous highly concentrated pigment slurry. Its distribution is insufficient. Sodium o-phenylphenolate in form of a powder has a pH value which is too high for many subsequent uses as do the corresponding alkaline solutions. Also, the powder form may not be handled easily in larger amounts. Liquid formulations are clearly preferred.

o-Phenylphenol in monopropylene glycol is not water miscible due to the poor solubility of o-phenylphenol and, therefore, may not be used as a preservative for pigment slurries in this formulation. Upon introduction into aqueous systems the solution precipitates as a greasy, tacky and fluffy substance. Aqueous sodium o-phenylphenolate of 25% by wt. as well as potassium o-phenylphenolate of 35% by wt. are very caustic and have a high pH value of above 12. Upon addition to an aqueous pigment slurry with high solids content, in particular with a solids concentration of >50% by volume, this high pH and the high ionic concentration lead to the formation of agglomerates in the pigment slurry and to an alteration of the pH in the final product.

The use of emulsified sodium o-phenylphenolate in pigment slurries with high solids content bears a risk since the emulsifying agent destabilizes the pigment dispersion and tends to foam formation. Furthermore, the freezing point of most of the aqueous salt solutions and aqueous emulsions of o-phenylphenol is at or slightly below 0° C. Only o-phenylphenol in propylene glycol and potassium o-phenylphenolate have a freezing point of <-15° C. However, these show the poor miscibility and the risk of formation of agglomerates, respectively. During the winter in Northern Europe, e.g. in Norway as well as in North America and Canada, it is impossible to transport aqueous solutions without the risk of freezing if no heating is present in the transport container. The same problem is encountered during storage.

SUMMARY OF THE INVENTION

It is an object of the present invention to provide a liquid formulation of phenol and/or phenol derivatives, in particular of o-phenylphenol, having a pH which may be adapted to final use. Furthermore, the formulation should have a freezing point of at least -7° C. Moreover, with respect to transport and storage costs the concentration of the solution of the phenol and/or phenol derivative, preferably the o-phenylphenol solution, should be as high as possible to reduce the transport and storage volume.

According to the invention, this object has been solved by an aqueous formulation containing phenol and/or phenol derivatives comprising partially neutralized phenol and/or partially neutralized phenol derivatives and one or more glycol compounds and/or glycerol.

The formulations of the present invention have a freezing point of at least -7° C. Preferred embodiments of the formulations have freezing points of -10° C. or even -15° C. Furthermore, using the formulation according to the invention the amounts of phenol and phenol derivatives may be preferably greater than 25% by wt.

A particularly great advantage of the formulation according to the invention is that the pH value thereof may be adjusted to the value required for the later use. Examples are pH values of 8.5–9.5 for calcium carbonate slurries, and 9.5–10.5 for talc slurries as well as 7.0–7.5 for American kaolin slurries. This is achieved because the phenol used according to the invention and/or the derivatives of phenol, preferably o-phenylphenol is present in a partially neutralized form, preferably in a form partially neutralized with alkali hydroxides. Particularly preferable, NaOH or KOH are used for partial neutralization.

Glycol compounds, preferably aliphatic glycol compounds and/or glycerol are employed as solution aid between phenol and water. At the same time, these substances act to lower the freezing points of the formulation (solution). Preferably, among the glycols 2- or 3-basic glycols are used. For example, glycols on the basis of ehtylene glycol, diethylene glycol or monopropylene glycol or mixtures thereof.

The phenol or the derivatives of phenol used according to the present invention have an anti-microbial effect and, thus, act as preservatives. Due to these properties, the formulation of the present invention may serve both for protective and curative uses.

Preferred phenol derivatives are mono- or polysubstituted phenols with aliphatic and/or aromatic substituents. Examples for such derivatives which may be used according to the invention are o-phenylphenol (OPP), halogenated phenols, cresols, halogenated cresols, resocinols and parahydroxybenzoic acid esters (PHB esters) or the mixtures thereof. Examples for cresols are halogenated cresols, in particularly chlorinated cresols, o-, m-, and p-cresol, isopropyl o-cresol, 4-isopropyl m-cresol. An example for a resorcinol which may be used is 4-n-hexyl resorcinol.

Most important for the success of the present invention is partial neutralization of the phenol and its derivatives. The degree of partial neutralization of phenol and its derivatives is in the range of 5–95 mole %, preferably 5–80 mole %. The preferred ranges especially depend on the pH ranges in which the formulations according to the invention will be used. For example, if they are used in a pH range of 6–8 the preferred degree of partial neutralization is 5–60 mole % and particularly preferred 5–30 mole %. For a later use in a pH range of 7–9 the degree of partial neutralization preferably is 20–50 mole %, for example 20–30 mole %. For a later use in a pH range of 8–10 the degree of partial neutralization preferably is 30–70 mole %, for example 30–50 mole %, and for a later use in a pH range of 9–11 the preferred degree of partial neutralization is 50–80 mole %, for example 50–70 mole %.

Phenol and/or its derivatives are present in the formulation in an amount of 5–50% by wt., more conveniently 15–40% by wt., and as the organic solvents aliphatic glycol compounds and/or glycerol in an amount of 20–90% by wt., preferably 40–80% by wt. and in addition optionally aromatic alcohols in an amount of 0–70% by wt., more conveniently 0–50% by wt. may be present in the formulation, the total amount of organic solvents being 40–90% by wt. and the balance to 100% by wt. in each case being alkali hydroxide and water.

In a preferred embodiment of the present invention, the formulation contains one or more aromatic alcohols. Preferably, compounds of the following formula are used as the aromatic alcohols:

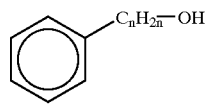

wherein optionally another substituent R is present in the o-, m- or p-position, where R is preferably a straight chain or branched aliphatic substituent having the formula —$C_nH_{2n+1}$, wherein n=1–5, preferably 1–3, further preferred 1.

Examples of alcohols which may be used are: benzyl alcohol and/or 2-phenylethane-1-ol and/or 3-phenylpropane-1-ol and/or 1-phenylpropane-2-ol or

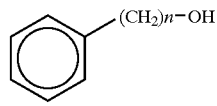

wherein n=1–5, preferably 1–3, further preferred 1.

In another embodiment of the present invention the formulation contains further substances with anti-microbial activity, for example compounds having anti-bacterial and/or anti-fungal activity. The preparation of the formulation according to the invention may be accomplished by the skilled artisan on the basis of his technical knowledge without any inventive step. For example, for the preparation of the formulation of the present invention, the phenol and/or its derivatives are dissolved in the glycol compound and/or the glycerol, preferably under gentle heating. However, the sequence may be reversed, i.e. first the phenol or the phenolic compound, respectively, is added followed by addition of the glycol compound or the glycerol, respectively. Following the preparation of the solution of phenol and/or the phenol derivative partial neutralization is achieved, preferably using an alkali hydroxide, which is added in a form dissolved in water. Aromatic alcohols may be included into the formulation as a further organic solvent. It is also possible to add other biocidal agents.

DETAILED DESCRIPTION OF THE INVENTION

In principle, as mentioned above the sequence of addition is all the same. However, there may be a temporary incompatibility leading to temporary precipitation of substances. Therefore, the phenol compounds are preferably dissolved in the organic solvent followed by addition of the partial neutralizing agent in the appropriate amount of water.

There has been surprisingly and unexpectedly found that phenol derivatives such as phenol, o-phenylphenol, cresols, partially neutralized with alkali hydroxides, preferably in glycol/water were not precipitated from the glycol and did not develop two phases even at a high solids content and very low temperature of e.g. −18° C., that the solutions were stable for months, a brown coloration such as that which has been for example well known from alkali salts of o-phenylphenol was much weaker and the freezing point and pH value could be adjusted according to need.

As may be seen also from the accompanying examples, the formulation according to the present invention will be preferably used as a preservative, particularly preferred for the preservation of aqueous suspensions or dispersions of minerals, fillers, pigments and natural or synthetic organic binders and the mixtures thereof. Furthermore, it may be employed in the preservation of coolants, preferably in the metal processing industry. Aqueous suspensions or dispersions of minerals, fillers and/or pigments containing the formulation according to the invention are preferably used in the fields of paper making, paper coating and aqueous varnishes and paints. It is suitable for protective as well as for curative use.

Moreover, the aqueous suspension or dispersion may contain one or more synthetic and/or natural organic binder(s), preferably styrene butadiene latexes and/or styrene acrylate latexes, starch and/or carboxymethylcellulose which are protected from microbial attack and/or spoilage.

As the minerals and/or fillers and/or pigments, the aqueous suspension or dispersion preferably contains elements of the second and/or third main group and/or the fourth main group and/or the fourth side group of the periodic system of the elements, particularly compounds and/or organic pigments containing calcium and/or silicon and/or aluminium and/or titanium and/or barium.

Preferably, the aqueous suspension or dispersion contains minerals and/or fillers and/or pigments containing kaolin and/or aluminium hydroxide and/or titanium dioxide and/or barium sulfate and/or polystyrene hollow spheres and/or formaldehyde resins and/or calcium carbonate, in particular natural calcium carbonates and/or precipitated calcium carbonates and/or marble and/or lime and/or dolomite and/or dolomite-containing calcium carbonates.

In the following, the invention will be explained further with respect to the examples also in comparison to the prior art. However, the invention is not limited to these representative embodiments.

General Comments with Respect to the Examples

1.) Germ Countings

The germ count was determined according to the method "Determination of aerobic mesophilic germs", Schweizerisches Lebensmittelbuch, chapter 56, paragraph 7.01, 1985 edition, revised version 1988. Mostly, the bacterial strains detected were from the family of pseudomonads (predominantly Pesudomonas aeruginosa).

2.) Measurement of the Viscosity of the Mineral and/or Filler and/or Pigment Suspension Measurement of the viscosity was performed on a Brookfield viscosimeter type PVF-100 at 100 rpm. The following spindles were used for the individual measurements:

| Spindle | RV2 | 40–320 mPas |
|---------|-----|-------------|
|         | RV3 | 320–800 mPas |
|         | RV4 | 800–1600 mPas |
|         | RV5 | 1600–3200 mPas |
|         | RV6 | 3200–8000 mPas |

The measurement was carried out in a low 400 ml beaker.

The temperature during the measurement was 20° C. The measurement was performed after 1 min of stirring.

Prior to the actual measurements, all samples were stirred intensively for 2 min (5000 rpm, stirring disc diameter 50 mm).

This type of viscosity measurement was used in all of the following examples.

3.) Fineness of the Mineral and/or Filler and/or Pigment Suspension

The fineness characteristics of the suspensions prepared according to the invention were determined by sedimentation analysis in a gravity field using a SEDIGRAPH 5100 from Micromeritics company, U.S.A.

Measurement of the cationically stabilized suspensions was carried out in distilled water. Dispersion of the samples was performed by rapid stirrer and sonication.

Powder measurements were performed in 0.1% $Na_4P_2O_7$ solution.

The particle distribution measured was depicted on a x-y recorder as the cumulative undersize frequency curve (see e.g. Belger, P., Schweizerische Vereinigung der Lack- und Farbenchemiker, XVII. FATIPEC-Kongress, Lugano, Sep. 23–28, 1984) the x-axis representing the particle diameter of a corresponding spherical cross section and the y-axis representing the amount of the particles in % by weight.

PRIOR ART EXAMPLES

Example 1

Prior Art

A 20% by wt. solution of o-phenylphenol was prepared by dissolving o-phenylphenol in distilled water with 1.05 moles NaOH/mole o-phenylphenol.

Result

Freezing point: −3° C.

The pH of the 20% by wt. solution of o-phenylphenol was 12.2 (measured at 20° C.). The pH of the solution diluted to 1% actives with water was 11.8.

If the pH was reduced to below 10.5 by slow addition of diluted acid (e.g. HCl) under agitation precipitation occurred and a partially neutralized o-phenylphenol solution may be prepared, respectively. The product forms a precipitate.

The pH may not be adjusted to the value necessary for final use. The freezing point is unacceptable.

If NaOH was used a neutralizing agent it was impossible to prepare o-phenylphenol solutions with concentrations of clearly above 20% by wt. at room temperature, or they already recrystallized during storage at room temperature.

Example 2

Prior Art

A 28% by wt. solution of o-phenylphenol was prepared by dissolving o-phenylphenol in distilled water with 1.1 moles KOH/mole o-phenylphenol.

Results

Freezing point: −16° C., crystallization starts at −13° C.

The pH of the 28% by wt. solution of o-phenylphenol was 12.6 (measured at 20° C.). The pH of the solution diluted to 1% actives with water was 12.1.

The freezing point is in the proper range, however, the product is useless because of its high pH value.

If the pH was reduced to below 10.5 by slow addition of diluted acid (e.g. HCl) under agitation precipitation occurred.

The pH can not be adjusted to the value necessary for final use and it is impossible to prepare a partially neutralized o-phenylphenol solution without precipitation.

Example 3

Prior Art

An aqueous slurry of kaolin from Georgia, USA having a solids content of 72.8% by wt. and a grain size distribution such that 94% by wt. of the particles had a diameter of below 2 mm (as measured by Sedigraph 5100, Micromeritics, USA) dispersed with 0.35% by wt. of sodium polyacrylate and a pH of 7.4 was preserved by 300 g actives of o-phenylphenol/t of slurry. Addition of o-phenylphenol according to example 1. (300 g actives of o-phenylphenol)/t slurry=about 1500 g 20% solution/t slurry)

A blank of the kaolin sample was prepared in the same manner but without preservative.

| | Results: | |
|---|---|---|
| | pH | Brookfield viscosity spindle 3, 100 rpm after preparation | Brookfield viscosity spindle 3, 100 rpm after 1 week |
| Blank without o-phenylphenol | 7.4 | 240 mPas | 330 mPas |
| Sample with 300 g o-phenylphenol/t | 8.1 | 310 mPas | 760 mPas |

In the blank without o-phenylphenol a germ count of $10^5$/g was measured after 24 hrs.

In the sample with 300 g o-phenylphenol/t a germ count <100/g was measured after 24 hrs.

Upon addition of the o-phenylphenol solution of example 1 and during a storage time of 1 week, the viscosity of the kaolin slurry wit h high solids content dispersed with sodium polyacrylate immediately increased. The pH of the slurry was changed upon addition of the o-phenylphenol solution of example 1.

In this case, there is a risk that it may be impossible to unload the slurry after shipment of several weeks in large amounts by ship, rail or truck. The pH of the final use, e.g., as a paint or in paper making, is affected.

To keep the slurry sterile, 300 ppm actives of o-phenylphenol of example 1 are necessary. The slurry may not be conserved without adversely affecting the other properties of the slurry.

Example 4

Prior Art

An aqueous slurry of calcium carbonate from natural marble of No rway having a solids content of 77.8% by wt. and a grain size distribution such that 90% by wt. of the particles had a diameter of below 2 mm (as measured by Sedigraph 5100, Micromeritics, USA) was preserved by 250 g actives of o-phenylphenol/t of slurry. Addition of o-phenylphenol according to example 2.

(250 g actives of o-phenylphenol)/t slurry=about 890 g 28% solution/t slurry)

A blank of the calcium carbonate slurry was prepared in the same manner but without preservative.

Results:

|  | pH | Brookfield viscosity spindle 3, 100 rpm after preparation | Brookfield viscosity spindle 3, 100 rpm after 1 week |
|---|---|---|---|
| Blank without o-phenylphenol | 9.6 | 340 mPas | 350 mPas |
| Sample with 250 g o-phenylphenol/t | 10.2 | 320 mPas | 460 mPas |

The screenings of the blank without o-phenylphenol as a potassium o-phenylphenol solution was 25 ppm on a screen with a mesh size of 45 μm.

The screenings of the sample with 250 ppm o-phenylphenol as a potassium o-phenylphenol solution was 160 ppm on a screen with a mesh size of 45 μm.

In the blank without o-phenylphenol a germ count of $10^5$/g was measured after 24 hrs.

In the sample with 250 g o-phenylphenol/t a germ count <100/g was measured after 24 hrs.

The viscosity of the calcium carbonate slurry having a high solids content dispersed with sodium polyacrylate was not very much increased during storage for 1 week. However, it was obvious that the screenings on the 45 μm screen were unacceptably increased. The pH of the slurry was harmfully changed into the more alkaline range.

A product of this type leads to scratches in the paper coat and to dusting during printing.

To preserve the slurry from spoilage by microorganisms, 250 ppm actives of o-phenylphenol of example 2 are necessary. The slurry may not be conserved without adversely affecting the other properties of the slurry.

INVENTIVE EXAMPLES

Example 5

A o-phenylphenol solution was prepared by dissolving 42.5 g o-phenylphenol and using 26.4 g monopropylene glycol, 5.5 g NaOH and 25.6 g water to obtain a 42.5% by wt. solution, based on o-phenylphenol.

The degree of neutralization of the phenolic group of o-phenylphenol with NaOH was 55 mole %.
Results
Freezing point: below −18° C.
At −18° C. the solution was still liquid, viscous and clear. No crystallization could be observed.

Example 6

A o-phenylphenol solution was prepared by dissolving 47.5 g o-phenylphenol and using 29.4 g monopropylene glycol, 3.5 g NaOH and 19.6 g water to obtain a 47.5% by wt. solution, based on o-phenylphenol.

The degree of neutralization of the phenolic group of o-phenylphenol with NaOH was 22.4 mole %.
Results
Freezing point: below −18° C.
At −18° C. the solution was still liquid, viscous and clear. No crystallization could be observed.

Example 7

A o-phenylphenol solution was prepared by dissolving 50.0 g o-phenylphenol and using 27 g monopropylene glycol, 1.0 g NaOH and 22.0 g water to obtain a 50% by wt. solution, based on o-phenylphenol.

The degree of neutralization of the phenolic group of o-phenylphenol with NaOH was 8.5 mole %.
Results
Freezing point: below −18° C.
At −18° C. the solution was still liquid, viscous and clear. No crystallization could be observed.

Example 8

A o-phenylphenol solution was prepared by dissolving 250 g o-phenylphenol using 500 g monopropylene glycol under gentle heating. Then, 30 g NaOH, dissolved in 220 g water, were added to obtain 1 kg of an approx. 25% by wt. solution, based on o-phenylphenol.

The degree of neutralization of the phenolic group of o-phenylphenol with NaOH was 51.1 mole %.
Results
Freezing point: below −18° C.
At −15° C. the solution was still liquid, viscous and clear. No crystallization could be observed.
At −10° C. the viscosity was only 460 mPas. Because of the low viscosity at −10° C. the product is pumpable also below the freezing point.

Example 9

A o-phenylphenol solution was prepared by dissolving 30 g o-phenylphenol using 45 g ethylene glycol, 6 g NaOH and 19 g water, were added to obtain 100 g of an approx. 30% by wt. solution, based on o-phenylphenol.

The degree of neutralization of the phenolic group of o-phenylphenol with NaOH was 85 mole %.
Results
Freezing point: below −18° C.
At −15° C. the solution was still liquid, viscous and clear. No crystallization could be observed.
At −10° C. the viscosity was only 840 mPas. Because of the low viscosity at −10° C. the product is pumpable also below the freezing point.

Example 10

An aqueous slurry of kaolin from Georgia, USA, having a solids content of 72.8% by wt. and a grain size distribution such that 94% by wt. of the particles had a diameter of below 2 mm (as measured by Sedigraph 5100, Micromeritics, USA) dispersed with 0.35% by wt. of sodium polyacrylate and a pH of 7.4 was preserved by 300 g actives of o-phenylphenol/t of slurry. Addition of o-phenylphenol according to example 7.

(300 g actives of o-phenylphenol)/t slurry=about 600 g 50% solution/t slurry)

268.5 g water in 2 liter beaker

Add 3.5 g sodium polyacrylate

Mix in 728 g of kaolin 15 min Dispersion at 2500 rpm stirring disc ø 50 mm

Add 0.600 g of the 50% solution under stirring;

all examples concerning the preparation of pigment slurry were prepared in this manner.

| | Results: | |
|---|---|---|
| | pH | Brookfield viscosity spindle 3, 100 rpm after preparation | Brookfield viscosity spindle 3, 100 rpm after 1 week |
| Blank without o-phenylphenol | 7.4 | 240 mPas | 330 mPas |
| Sample with 300 g o-phenylphenol/t | 7.4 | 250 mPas | 350 mPas |

In the blank without o-phenylphenol a germ count of $10^5$/g was measured after 24 hrs.

In the sample with 300 g o-phenylphenol/t a germ count <100/g was measured after 24 hrs.

The viscosity of the kaolin slurry with high solids content dispersed with sodium polyacrylate was stable during a storage time of 1 week. The pH of the slurry was remarkably constant.

In this regard and under these circumstances, there is no risk that it may be impossible to unload the slurry after shipment of several weeks in large amounts by ship, rail or truck.

The other properties of the slurry are not adversely affected by the solution according to the invention of example 7 as compared to example 3 of the prior art.

Example 11

An aqueous slurry of calcium carbonate from natural ground marble of Norway having a solids content of 77.8% by wt. and a grain size distribution such that 90% by wt. of the particles had a diameter of below 2 mm (as measured by Sedigraph 5100, Micromeritics, USA) was preserved by 250 g actives of o-phenylphenol/t of slurry. Addition of o-phenylphenol according to example 8.

(250 g actives of o-phenylphenol)/t slurry about=525 g 47.5% solution/t slurry)

A blank of the calcium carbonate slurry was prepared in the same manner but without preservative.

| | Results: | |
|---|---|---|
| | pH | Brookfield viscosity spindle 3, 100 rpm after preparation | Brookfield viscosity spindle 3, 100 rpm after 1 week |
| Blank without o-phenylphenol | 9.6 | 340 mPas | 350 mPas |
| Sample with 250 g o-phenylphenol/t | 9.5 | 350 mPas | 380 mPas |

The screenings of the blank without the novel biocide was 28 ppm on a screen with a mesh size of 45 μm.

The screenings of the sample with the novel biocide was 31 ppm on a screen with a mesh size of 45 μm.

In the blank a germ count of $10^6$/g was measured after 24 hrs.

In the sample with 250 g o-phenylphenol/t a germ count <100/g was measured after 24 hrs.

The viscosity of the calcium carbonate slurry having a high solids content dispersed with sodium polyacrylate was stable during storage for 1 week. The pH of the slurries was remarkably constant.

The screenings were not adversely affected by the biocide, i.e. no aggregation took place.

The other properties of the slurry were not adversely affected by the solution according to the invention of example 8 as compared to example 1 of the prior art.

Example 12

An aqueous slurry of talc from Finland having a solids content of 64.2% by wt. and a grain size distribution such that 54% by wt. of the particles had a diameter of below 2 mm (as measured by Sedigraph 5100, Micromeritics, USA) dispersed with 0.25% by wt. of sodium polyacrylate and with 1.4% by wt. of a commercial ethylene oxide/propylene oxide adduct as detergent and 0.08% NaOH and a pH of 10.1 was preserved by 350 g actives of o-phenylphenol/t of slurry. Addition of o-phenylphenol according to example 9 as 30% solution.

(350 g actives of o-phenylphenol)/t slurry=1166.6 g 30% solution/t slurry)

| | Results: | |
|---|---|---|
| | pH | Brookfield viscosity spindle 3, 100 rpm after preparation | Brookfield viscosity spindle 3, 100 rpm after 1 week |
| Blank without o-phenylphenol | 10.1 | 320 mPas | 480 mPas |
| Sample with 350 g o-phenylphenol/t | 10.2 | 320 mPas | 540 mPas |

In the blank a germ count of $10^5$/g was measured after 24 hrs.

In the sample with 350 g o-phenylphenol/t a germ count <100/g was measured after 24 hrs.

The viscosity of the talc slurry with high solids content dispersed with sodium polyacrylate was nearly stable during a storage time of one week. The pH of the slurry was remarkably constant.

Under these circumstances, there is no risk that it may be impossible to unload the slurry after shipment of several weeks in large amounts by ship, rail or truck.

The other properties of the slurry are not adversely affected by the preservative according to the invention.

Example 13

An aqueous emulsion of oil in water was prepared similar to those used as coolants in metal processing having an emulsified oil content of 5% by wt. was preserved with 2 kg acitves of o-phenylphenol/t 5% coolant.

(2 kg actives of o-phenylphenol/t 5% coolant=approx. 4 kg 50% solution/t 5% coolant)

A blank was prepared in the same manner but without preservative.

| Results: | |
| --- | --- |
| | pH |
| Blank without o-phenylphenol | 6.9 |
| Sample with 2 kg o-phenylphenol/t | 7.0 |

In the blank a germ count of $10^7$/g was measured after 24 hrs.

In the sample with 2 kg o-phenylphenol/t coolant a germ count <100/g was measured after 24 hrs.

Despite of the high amount of preservative required the pH of the coolant was not affected by the partial neutralization of o-phenylphenol according to the invention.

Example 14

A phenol solution was prepared by dissolving 25 g of phenol using 45 g monopropylene glycol, 25 g ethylene glycol, 1 g NaOH and 24 g water to obtain 100 g of an approx. 25% by wt. solution, based on phenol.
Results
 Freezing point: below −18° C.
 At −15° C. the solution was still liquid, viscous and clear. No crystallization could be observed.
 At −10° C. the viscosity was <500 mPas. Because of the low viscosity at −10° C. the product is a pumpable also below the freezing point of water.

Example 15

A m-cresol solution was prepared by dissolving 25 g of m-cresol using 50 g monopropylene glycol, 2 g NaOH and 23 g water to obtain 1 kg of an approx. 25% by wt. solution, based on m-cresol.
Results
 Freezing point: below −18° C.
 At −15° C. the solution was still liquid, viscous and clear. No crystallization could be observed.
 At −10° C. the viscosity was <500 mPas. Because of the low viscosity at −10° C. the product is pumpable also below the freezing point of water.

Example 16

A phenol solution was prepared by dissolving 20 g of phenol using 20 g monopropylene glycol, 20 g ethylene glycol, 20 g of benzyl alcohol, 1 g NaOH and 19 g water to obtain 100 g of an approx. 20% by wt. solution, based on phenol. The degree of neutralization of the phenol with NaOH was 11.7 mole %.
Results
 Freezing point: below −18° C.
 At −15° C. the solution was still liquid, viscous and clear. No crystallization could be observed.
 At −10° C. the viscosity was <500 mPas. Because of the low viscosity at −10° C. the product is pumpable also below the freezing point of water.

Example 17

A solution of o-phenylphenol/2-methyl-4-isothiazolinone was prepared by dissolving 25 g of o-phenylphenol and 12.5 g 2-methyl-4-isothiazolinone using 20 g monopropylene glycol and 20 g benzyl alcohol and 2.5 g NaOH and 20 g water to achieve a 25% by wt. solution, based on o-phenylphenol and a 12.5% solution, based on MIT. The degree of neutralization of the phenolic groups of o-phenylphenol with NaOH was approx. 43.5 mole %.
Results
 Freezing point: below −18° C.
 At −18° C. the solution was still liquid, viscous and clear. No crystallization could be observed.

Example 18

A solution of o-phenylphenol was prepared by dissolving 25 g of o-phenylphenol using 50 g mondpropylene glycol, 75 g benzyl alcohol, 1 g NaOH and 24 g water to achieve 175 g of an approx. 14.5% by wt. solution, based on o-phenylphenol. The degree of neutralization of the phenolic groups of o-phenylphenol in this example was approx. 17.5 mole %.

In this example, the amount of benzyl alcohol was about 43% by wt. Therefore, the ratio of OPP:benzyl alcohol was about 1:3 on a weight basis.
Results
 Freezing point: below −20° C.
 At −20° C. the solution was still liquid and clear. No crystallization could be observed. The viscosity was 280 mPas. Due to the low viscosity at −20° C. the product is also easily pumpable below the freezing point of water. The color of the solution was light yellow.

What is claimed is:

1. Aqueous suspension or dispersion of minerals, fillers or pigments, comprising an aqueous antimicrobial agent, the, aqueous antimicrobial agent comprising a phenol derivative in a partially neutralized form as well as an organic solvent comprising one or more members selected from the group consisting of a glycol compound and glycerol, wherein the partially neutralized phenol derivative is present in the aqueous antimicrobial agent in an amount of at least 25% by weight.

2. Suspension or dispersion according to claim 1, wherein the phenol derivative is a monosubstituted phenol or polysubstituted phenol with an aliphatic or aromatic substituent, and the glycol compound is an aliphatic glycol compound.

3. Suspension or dispersion according to claim 1, wherein the phenol derivative is one or more members selected from the group consisting of o-phenylphenol, halogenated phenol, cresol, halogenated cresol, resorcinol, and parahydroxybenzoic ester.

4. Suspension or dispersion according to claim 3, wherein the cresol is o-cresol, m-cresol, p-cresol, isopropyl-o-cresol, 4-isopropyl-m-cresol, or halogenated cresol.

5. Suspension or dispersion according to claim 4, wherein the halogenated cresol is chlorinated cresol.

6. Suspension or dispersion according to claim 3, wherein the resorcinol is 4-n-hexylresorcinol.

7. Suspension or dispersion according to claim 2, wherein the aliphatic glycol compound is one or more members selected from the group consisting of ethylene glycol, monopropylene glycol, and diethylene glycol.

8. Suspension or dispersion according to claim 1, wherein said phenol derivative is present in a form partially neutralized by an alkali hydroxide.

9. Suspension or dispersion according to claim 1, wherein said phenol derivative in the antimicrobial agent is partially neutralized by KOH or NaOH.

10. Suspension or dispersion according to claim 1, wherein said phenol derivative in the antimicrobial agent is present in a form partially neutralized at a degree of 5–95 mole %.

11. Suspension or dispersion according to claim 10, wherein the degree is 5–80 mole %.

12. Suspension or dispersion according to claim 10, wherein the degree is 5–60 mole %, wherein the pH value thereof can be adjusted for later use in a pH range of 6–8.

13. Suspension or dispersion according to claim 10, wherein the degree is 5–30 mole %, wherein the pH value thereof can be adjusted for later use in a pH range of 6–8.

14. Suspension or dispersion according to claim 10, wherein the degree is 20–50 mole %, wherein the pH value thereof can be adjusted for later use in a pH range of 7–9.

15. Suspension or dispersion according to claim 10, wherein the degree is 20–40 mole %, wherein the pH value thereof can be adjusted for later use in a pH range of 7–9.

16. Suspension or dispersion according to claim 10, wherein the degree is 30–70 mole %, wherein the pH value thereof can be adjusted for later use in a pH range of 8–10.

17. Suspension or dispersion according to claim 10, wherein the degree is 30–50 mole %, wherein the pH value thereof can be adjusted for later use in a pH range of 8–10.

18. Suspension or dispersion according to claim 10, wherein the degree is 50–80 mole %, wherein the pH value thereof can be adjusted for later use in a pH range of 9–11.

19. Suspension or dispersion according to claim 10, wherein the degree is 50–70 mole %, wherein the pH value thereof can be adjusted for later use in a pH range of 9–11.

20. Suspension or dispersion according to claim 1, wherein the antimicrobial agent further contains one or more aromatic alcohols.

21. Suspension or dispersion according to claim 1, wherein the partially neutralized phenol derivative is present in the aqueous antimicrobial agent in an amount of 25–50% by weight, water is present in an amount of at least 19% by weight, alkali hydroxide is present in an amount of at least 1% by weight, and the balance to 100% by weight is organic solvent.

22. Suspension or dispersion according to claim 20, wherein the aromatic alcohol has the following formula:

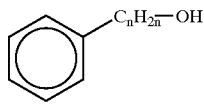

wherein n=1–5.

23. Suspension or dispersion according to claim 22, wherein n=1–3.

24. Suspension or dispersion according to claim 22, wherein another substituent R is present in positions o, m, or p, wherein R is a straight chain or branched aliphatic substituent having the formula $C_nH_{2n+1}$, and wherein n=1–5.

25. Suspension or dispersion according to claim 24, wherein n=1–3.

26. Suspension or dispersion according to claim 20, wherein the aromatic alcohol is one or more members selected from the group consisting of benzyl alcohol, 2-phenylethane-1-ol, 3-phenylpropane-1-ol, 1-phenylpropane-2-ol, and

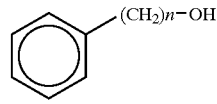

wherein n=1–5.

27. Suspension or dispersion according to claim 26, wherein n=1–3.

28. Suspension or dispersion according to claim 1, wherein said partially neutralized phenol derivative is present in the aqueous antimicrobial agent in an amount of 25–40% by weight, water is present in an amount of at least 19% by weight, alkali hydroxide is present in an amount of at least 1% by weight, and the balance to 100% by weight is organic solvent.

29. Suspension or dispersion according to claim 28, further comprising an aromatic alcohol having the following formula:

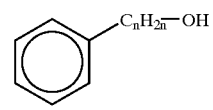

wherein n=1–5.

30. Suspension or dispersion according to claim 29, wherein n=1–3.

31. Suspension or dispersion according to claim 29, wherein another substituent R is present in positions o, m, or p, wherein R is a straight chain or branched aliphatic substituent having the formula $C_nH_{2n+1}$, and wherein n=1–5.

32. Suspension or dispersion according to claim 31, wherein n=1–3.

33. Suspension or dispersion according to claim 28, further comprising an aromatic alcohol selected from the group consisting of benzyl alcohol, 2-phenylethane-1-ol, 3-phenylpropane-1, 1-phenylpropane-2-ol, and

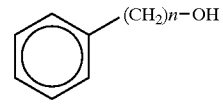

wherein n=1–5.

34. Suspension or dispersion according to claim 33, wherein n=1–3.

35. Suspension or dispersion according to claim 1, wherein the aqueous antimicrobial agent contains at least one additional substance with antimicrobial activity.

36. Suspension or dispersion according to claim 1, wherein the glycol compound or glycerol is, present in the aqueous antimicrobial agent in an amount of at least 20% by weight.

37. A method of preparing a compound for use in paper making, paper coating, aqueous lacquers, varnishes, or paints, the method comprising:

(a) providing an aqueous suspension or dispersion of minerals, fillers or pigments comprising an aqueous antimicrobial agent, the aqueous antimicrobial agent comprising a phenol derivative in a partially neutralized form as well as an organic solvent comprising one or more members selected from the group consisting of a glycol compound and glycerol wherein the partially neutralized phenol derivative is present in the aqueous antimicrobial agent in an amount of at least 25% by weight; and (b) preparing a compound for use in paper making, paper coating, aqueous lacquers, varnishes, or paints by incorporating therein an aqueous suspension or dispersion of step (a).

* * * * *